United States Patent [19]
Pettit et al.

[11] Patent Number: 5,426,194
[45] Date of Patent: Jun. 20, 1995

[54] ISOLATION AND STRUCTURE OF HALISTATIN 1

[75] Inventors: George R. Pettit, Paradise Valley; Rui Tan; Feng Gao, both of Tempe, all of Ariz.

[73] Assignee: Arizona Board of Regents, a body corporate acting on behalf of Arizona State University, Tempe, Ariz.

[21] Appl. No.: 4,851

[22] Filed: Jan. 19, 1993

[51] Int. Cl.⁶ .......................................... C07D 323/00
[52] U.S. Cl. .................................................. 549/267
[58] Field of Search ........................ 549/267; 514/450

Primary Examiner—C. Warren Ivy
Assistant Examiner—A. A. Owens
Attorney, Agent, or Firm—Richard R. Mybeck

[57] ABSTRACT

An intensive long-term investigation of marine organisms as sources of new anticancer drugs has led to the isolation and structural elucidation (primarily by high field NMR and mass spectrometry) of halistatin 1, a new polyether macrolide of the halipyran-type, from the Western Indian Ocean sponge *Phakellia carteri*. Halistatin 1 ($8.8 \times 10^{-7}$% yield) caused the accumulation of cells arrested in mitosis, inhibited tubulin polymerization, and inhibited the binding of radiolabeled vinblastine and GTP to tubulin.

1 Claim, 1 Drawing Sheet

| NATIONAL CANCER INSTITUTE DEVELOPMENTAL THERAPEUTICS PROGRAM MEAN GRAPHS | | | | | | | |
|---|---|---|---|---|---|---|---|
| PANEL/CELL LINE | | LOG₁₀ GI50 | GI50 | PANEL/CELL LINE | | LOG₁₀ GI50 | GI50 |
| LEUKEMIA | CCRF-CEM | −9.43 | | CNS CANCER | SF-268 | −8.66 | |
| | HL-60(TB) | −9.48 | | | SF-295 | −9.96 | |
| | K-562 | −9.44 | | | SF-539 | −9.44 | |
| | MOLT-4 | −9.21 | | | SNB-19 | −8.64 | |
| | RPMI-8226 | −9.32 | | | SNB-75 | −9.54 | |
| | SR | −9.43 | | | SNB-78 | −9.32 | |
| | SR | −9.77 | | | U251 | −9.29 | |
| | | | | | XF 498 | −9.32 | |
| NON-SMALL CELL LUNG CANCER | A549/ATCC | −8.54 | | MELANOMA | LOX IMVI | −10.09 | |
| | EKVX | −8.33 | | | MALME-3M | −9.68 | |
| | HOP-18 | −8.00 | | | M14 | −9.21 | |
| | HOP-62 | −9.08 | | | M19-MEL | −9.64 | |
| | HOP-92 | −8.96 | | | SK-MEL-2 | −9.54 | |
| | NCI-H226 | −9.09 | | | SK-MEL-28 | −9.11 | |
| | NCI-H23 | −9.24 | | | SK-MEL-5 | −9.80 | |
| | NCI-H322M | −8.46 | | | UACC-257 | −9.07 | |
| | NCI-H460 | −9.40 | | | UACC-62 | −9.57 | |
| | NCI-H522 | −9.68 | | OVARIAN CANCER | IGROVI | −9.08 | |
| | LXFL 529 | −9.32 | | | OVCAR-3 | −9.60 | |
| SMALL CELL LUNG CANCER | | | | | OVCAR-4 | −8.15 | |
| | | | | | OVCAR-5 | −9.31 | |
| | DMS 114 | −9.48 | | | OVCAR-8 | −8.72 | |
| | DMS 273 | −9.54 | | | SK-OV-3 | −9.33 | |
| COLON CANCER | COLO 205 | −9.37 | | RENAL CANCER | 786-0 | −9.16 | |
| | DLD-1 | −8.92 | | | A498 | −8.85 | |
| | HCC-2998 | −8.89 | | | ACHN | −8.49 | |
| | HCT-116 | −9.30 | | | CAKI-1 | −8.80 | |
| | HCT-15 | −8.38 | | | RXF-393 | −9.52 | |
| | HT29 | −9.38 | | | SN12C | −8.66 | |
| | KM12 | −9.24 | | | TK-10 | −8.22 | |
| | KM20L2 | −9.28 | | | UO-31 | −8.21 | |
| | SW-620 | −9.40 | | | MG MID | −9.15 | |
| | | | | | DELTA | −0.94 | |
| | | | | | RANGE | −2.09 | |
| | | | +1 0 −1 | | | | +1 0 −1 |

ISOLATION AND STRUCTURE OF HALISTATIN 1

INTRODUCTION

This invention relates generally to a newly discovered compound which is found to inhibit the growth of various selected cell lines which have been identified by the National Cancer Institute to cause cancer in human beings. More specifically, this invention relates to a new polyether macrolide antimitotic agent denominated "Halistatin 1" which was first isolated from *Phakellia carteri*. Hallistatin 1 is found to cause the accumulation of cells arrested in mitosis, inhibit tubulin polymerization, inhibit the binding of radiolabeled vinblastine and GTP to tubulin, to demonstrate an $ED_{50}$ of $4 \times 10^{-4}$ $\mu g/mL$ against the NCI's P388 cell line using the NCI protocol, and to demonstrate effectiveness against NCI human cancer cell lines.

Financial assistance for this project was provided by U.S. Government Grant No. OIG-CA-44344-01-A1-02. The United States Government may own certain rights in this invention.

BACKGROUND OF THE INVENTION

A great number of ancient marine invertebrate species in the Phyla Bryozoa, Mollusca and Porifera were well established in the earth's oceans over one billion years ago. Certainly such organisms had explored trillions of biosynthetic reactions in their evolutionary chemistry to reach present levels of cellular organization, regulation and defense. Marine sponges have changed minimally in physical appearance for nearly 500 million years, suggesting a very effective chemical evolution in response to changing environmental conditions for at least the time period under consideration. Some recognition of the potential for utilizing biologically potent marine animal constituents was recorded in Egypt about 2,700 BC, and by 200 BC sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and/or cytotoxic agents. Analogous considerations suggested that marine organisms could also provide effective new drugs for other severe medical challenges, such as viral diseases. Furthermore, marine organisms were expected to contain potentially useful drug candidates (and biochemical probes) of unprecedented structural types that would have eluded discovery by contemporary techniques of medicinal chemistry. Fortunately, some of these expectations have been realized in the intervening period. Illustrative of these successes are the discoveries of the bryostatins, dolastatins, and cephalostatins by the Cancer Research Institute at Arizona State University, Tempe, Arizona where five members of these remarkable anticancer drug candidates are either now in human clinical trial or preclinical development. See U.S. Pat. Nos. 4,816,444; 4,833,257; 4,873,245 and 4,879,278.

As is well known to those presently engaged in medical research, the time between the isolation of a promising new compound and its availability in the market place takes at least several years in the best case and can take several decades when an entity to finance the tortuous regulatory trail is slow to appear. Consequently, industry, in association with the government, has devised a number of qualifying tests which serve two purposes. One purpose is to eliminate those substances whose results in the qualifiers unequivocally demonstrate that the further expenditure of funds on developing those substances would be economically counterproductive. The second, and more important purpose, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such data approaches Ten Million Dollars ($10,000,000 U.S.) per substance. Basic economics dictate that such an investment will not be made unless there is a reasonable likelihood that it can be recovered. Absent such an opportunity, there will be no such investment, and without investment, research requisite for the discovery of potentially life saving drugs will stop.

Only two hundred years ago, many diseases ravaged humankind. Many of these diseases have been controlled or eradicated. In the development of the means to treat or control these diseases, work with the appropriate common experimental animals is of critical importance. With the various types of cancers, and with the HIV virus, such work is presently ongoing. The research for the treatment of various types of cancer is coordinated in the United States by the National Cancer Institute (NCI). NCI, as a government entity, has been charged with assisting all anti-cancer research. To establish whether a substance has anti-cancer activity, NCI has established a variety of protocols one of which involves testing the candidate substance against a cell line panel containing 60 human tumor cell lines. This protocol has been verified, and is generally accepted throughout the scientific community. This protocol and the established statistical means of evaluating the results obtained therefrom have been fully described in the literature See *Principles & Practice of Oncology* PPO Updates, Volume 3, Number 10, October 1989, by Michael R. Boyd, M.D., Ph.D. for an in depth description of the test protocol. The statistical analysis of the values obtained is explained in "Display and Analysis of Patterns of Differential Activity of Drugs Against Human Tumor Cell Lines: Development of Means Graph and COMPARE Algorithm", *Journal of the National Cancer Institute* Reports Vol. 81, No. 14, Pg. 1088, Jul. 14, 1989, by K. D. Paull et al. Both of these references are incorporated herein by this reference thereto.

The Constitution of the United States (Art. 1, Sec. 8) authorizes Congress to establish the United States Patent and Trademark Office (USPTO) to promote scientific advancement. This obligation can only be fully met when the USPTO accepts current medical and scientific realities in the area of medical research. The cell line identifiers designated by the NCI measure the activity of impairment of human tumor cell growth of a candidate drug. These values demonstrate "utility". The sole right obtained by the grant of Letters Patent is the prevention of others from exploiting the subject matter of the patent. The recognition of antineoplastic activity as statutory utility can aid research in the United States, and prevent the citizens of the United States from being held hostage by foreign governments or foreign corporations, if such research is no longer viable in the United States.

A major component of vigorous efforts for over two decades has been directed at marine sponge antineoplastic and/or cytotoxic biosynthetic products. The present disclosure reports the isolation and structural elucidation of a new, strongly cytotoxic macrolide herein denominated "halistatin 1".

BRIEF SUMMARY OF THE INVENTION

An intensive long-term investigation of marine organisms as sources of new anticancer drugs has led to the isolation and structural elucidation (primarily by high field NMR and mass spectrometry) of halistatin 1, a new polyether macrolide of the halipyran-type, from the Western Indian Ocean sponge *Phakellia carteri* the structure of which is shown below. Halistatin 1 (8.8 $\times 10^{-7}$% yield) caused the accumulation of cells arrested in mitosis, inhibited tubulin polymerization, inhibited the binding of radiolabeled vinblastine and GTP to tubulin, and demonstrated and $ED_{50}$ of $4\times10^{-4}$ µg/mL against the P388 cell line.

Accordingly, a principal object of the present invention is the isolation of a new polyether macrolide denominated "halistatin 1" having antimitotic properties.

Another object of the present invention is the structural elucidation of the substance denominated "halistatin 1".

These and still further objects as shall hereinafter appear are readily fulfilled by the present invention in a remarkably unexpected manner as will be readily discerned from the following detailed description of an exemplary embodiment thereof.

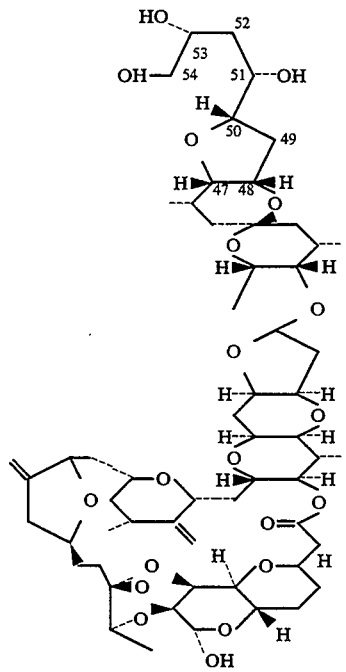

DESCRIPTION OF THE PREFERRED EMBODIMENT

A 1987 collection (250 kg. wet wt) of the orange sponge *Phakellia carteri* was made and stored in methanol. In 1989, the liquid phase was removed and diluted with dichloromethane followed by water. The dichloromethane fraction was separated by partition between hexane and methanol-water (9:1) followed by partition between dichloromethane and methanol-water (3:2). The cytostatic activity was located in the dichloromethane fraction ($ED_{50}$ 0.22 µg/mL, Scheme 1). The resulting PS cell line active ($ED_{50}$ 0.22 µg/mL) dichloromethane fraction was then separated by a series of gel permeation (methanol) and partition column chromatography on SEPHADEX LH-20, followed by HPLC on RP-8 reversed phase silica gel in the following manner.

Separation (Schemes 1-2) of the bioactive dichloromethane fraction by bioassay-directed (PS) SEPHADEX LH-20 column chromatography was conducted beginning with gel permeation (methanol) followed by partition (3:2 dichloromethane-methanol and hexane-toluene-methanol 3:1:1) sequences. Three PS active fractions (I, II, and III) from the latter chromatograms were identified (See: Scheme 1 below). Fraction III (2.5 g, $ED_{50}$ 0.03 µg/mL) was separated (Scheme 2) three times on a SEPHADEX LH-20 column with hexane-2-propanol-methanol (8:1:1), hexane-ethyl acetate-methanol (9:2:1) and heptane-chloroform-ethanol (7:4:1) as eluent to yield fraction C4 (10 mg) with PS $ED_{50}$ 0.0029 µg/ml. Further separation of fraction C4 was realized by reversed phase silica gel HPLC with methanol-acetonitrile-water (5:5:6) and detection by refractive index. The major component exhibited a sharp peak and represented halistatin 1 (2 mg, $8.8\times10^{-7}$% yield).

The structure elucidation of halistatin 1 was mainly accomplished by 2D NMR (Table 1) and mass spectral analyses. The molecular formula $C_{60}H_{86}O_{20}$ was established by high resolution mass spectrometry which revealed 1126 as the molecular weight with the molecular ion peak at 1149.5621 [M+Na]: Calcd. for $C_{60}H_{86}O_{20}Na$, 1149 5632 The IR spectrum showed carbonyl absorption at 1736 cm$^{-1}$ unconjugated double bonds at 1653 cm$^{-1}$ (sharp, weak) and ether absorptions at 1186, 1080 and 1018 cm$^{-1}$ (strong). Comprehensive analysis of $^1$H-NMR, $^1$H-$^1$H COSY, APT, HMQC and $^{13}$C-NMR spectra located 4 methyl groups ($\delta$0.96/18.15; 1.01/18.35; 1.05/15.84; 1.09/18.42), 19 methylenes (one attached directly to oxygen at $\delta$3.52, 3.45/67.20, 28 methines (24 bonded to oxygens), 2 vinylidene units ($\delta$5.07, 5.01/105.70; 4.87, 4.81/104.80; 153.33; 153.22), 4 quaternary carbons and 1 carbonyl group. These interpretations suggested a polyether macrolide Skeleton assembled reminiscent of the halichondrin series.

The structure of the compound denominated herein as halistatin 1 is as follows:

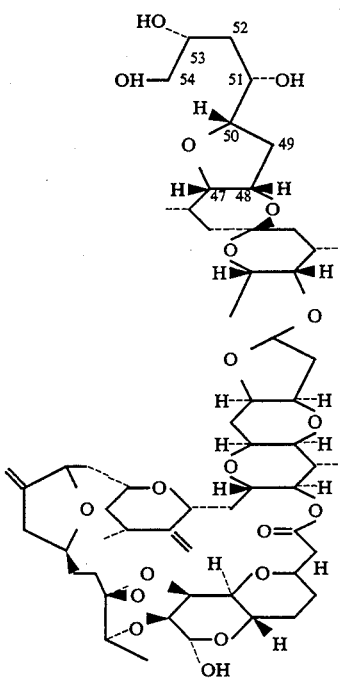

The ¹H-NMR spectrum of halistatin 1 superficially resembled that of halichondrin B. In the ¹H-¹H COSY spectrum of halistatin 1, the signal at δ 4.74 (triplet, J=4.6Hz) evidenced couplings with the signal at δ 4.25 (broadened doublet, J=4.4 Hz) and an upfield signal at δ 1.96 (doublet of doublets, J=13.3,4.6Hz) (Table 1). The latter signal showed strong coupling with another upfield signal at δ 2.12 (broadened doublet, J=13 Hz). From the chemical shift, coupling pattern and coupling constants, the signal at δ 4.74 was attributed to H-12 and the signals at δ 1.96 and 2.12 to H-13. In the COSY spectrum, the coupling pattern and chemical shift of the signals at δ 4.25 and δ 3.75 (doublet of doublets, J=4.3, 1.5 Hz) suggested that the C-10 proton was missing. Such an analysis was supported by the ¹³C NMR spectrum where a new quaternary carbon signal attributed to a hemiketal was observed at δ 103.75. In agreement with a hemiketal group at C-10, signals for the C-9 and C-11 carbons were shifted downfield (δ 6.5 ppm and 3.8 ppm, respectively). In the ¹H-NMR spectrum, the signals for H-9 and H-11 showed 0.4 ppm and 0.35 ppm upfield shifts respectively. The ¹H- and ¹³C-NMR signals for the other atoms were essentially the same as those of halichondrin B. H-11 showed small couplings with H-9 (δ 3.75) and one of the two H-13 (δ 2.12) protons, which were explained by W-couplings. Indeed, a Dreiding molecular model indicated that W-couplings should be present between H-11 and H-9, as well as between H-11 and one of the H-13 protons. An HMBC spectrum recorded at 500 MHz also strongly supported the structure assigned herein to halistatin 1. The ¹³C signal at δ 103.75 (C-10) showed a correlation with ¹H signals at δ 3.75 (H-9), 4.25 (H-11), 4.23 (H-8), and 4.74 (H-12). The ¹³C signals at δ 87.64 (C-11) showed cross peaks at δ 3.75 (H-9) 2.12 (H-13) 4.74 (H-12), Furthermore, the ¹³C signal at δ110.83 (c-14) showed cross peaks at 4.25 (H-11), 4.74 (H-12), 1.96 and 2.12 (H-13), and δ 4.23 (H-8). Other cross peaks agreed with the proposed structure (See Table 1 for details). No attempt was made to assign every methylene signal due to severe overlapping of the ¹H signals. However, ¹³C signals for 18 methylene groups in the δ 50 to 28 ppm region were observed. The asymmetric centers of halistatin 1 were assumed to be the same as those of halichondrin B. The optical rotation was similar, $[\alpha]_D = -58.4°$ (Lit. $-58.9°$ for halichondrin B as described by Uemura et al. in *Pure Appl. Chem.* 1986, 58, 701-710); since Dreiding molecular models indicated that a β-hydroxyl group was not sterically possible in such a condensed ring system, the hydroxyl group at the C-10 was assigned the α-orientation to complete the structural elucidation of halistatin 1. In turn, this overall assignment is based on an x-ray crystal structure determination of a norhalichondrin derivative. Due to the increasing importance and frequency of occurrence of the halichondrins the name halipyran was assigned to the unsubstituted ring system (A).

With L1210 murine leukemia cells, halistatin 1 and halichondrin B had similar cytotoxicity (IC$_{50}$ values of 0.5 and 0.2 nM, respectively), and both agents caused a significant rise in the mitotic index at cytotoxic concentrations, reaching values as high as 21% for halistatin 1. In the glutamate-induced polymerization of purified tubulin, performed as described by Bai et al. in *J. Biol Chem* 1991, 266, 15882-15889, halistatin 1 was slightly more active than halichondrin B (IC$_{50}$ values of 4.6+−0.4 and 4.9+−0.5 μM, respectively). Halichondrin B has been shown to be a noncompetitive inhibitor of the binding of radiolabeled vinblastine to tubulin and to inhibit nucleotide exchange on tubulin. A comparison of halistatin 1 to halichondrin B showed halistatin 1 had activity comparable to halichondrin B as an inhibitor of vinblastine binding, and that halistatin 1 was superior as an inhibitor of nucleotide exchange. Comparing the two drugs at 5 and 10 μM, halistatin 1 inhibited the binding of radiolabeled vinblastine by 57 and 73% at the two concentrations, as compared with 51% and 73% with halichondrin B. For radiolabeled GTP binding to tubulin, the same drug concentrations inhibited the reaction by 12% and 37% with halistatin 1, and by 14% and 18% with halichondrin B. Comparable values obtained previously with halichondrin B did not differ significantly from those obtained in the current studies. When tested in the U.S. National Cancer Institute's in vitro primary screen, (See: Boyd, M. R. Status of the NCI preclinical antitumor drug discovery screen: Implications for selection of new agents for clinical trial. In CANCER: Principles and Practice of Oncology Updates, Vol. 3, No. 10; DeVita, V. T., Jr., Hellman, S.; Rosenberg, S. A., Ed.; J. B. Lippincott: Philadelphia, 1989, pp 1-12; Monks, A.; Scudiero, D.; Skehan, P.; Shoemaker, R.; Paull, K.; Vistica, D.; Hose, C; Langley, J.; Cronise, P.; Vaigro-Wolff, A; Gray-Goodrich, M.; Campbell, H.; Boyd, M. *J. Natl, Cancer Inst.* 1991, 83, 757-766; Boyd, M. R.; K. D.; Rubinstein, L. R. Data display and analysis strategies for the NCI disease-oriented in vitro antitumor drug screen. In Antitumor Drug Discovery and Development; Valeriote, F. A.; Corbett, T.; Baker, L.Eds.; Kluwer Academic Publishers: Amsterdam, 1991, pp. 11-34.) Halistatin 1 yielded a pattern of differential cellular growth inhibition which was highly characteristic and of comparable potency to the halichondrins. Computerized pattern-recognition analyses revealed that the mean graph profiles of halistatin 1 and halichondrin B and homohalichondrin B were all strongly correlated with each other and also with the profiles of a general class of tubulin-interactive antimitotics.

SCHEME 1

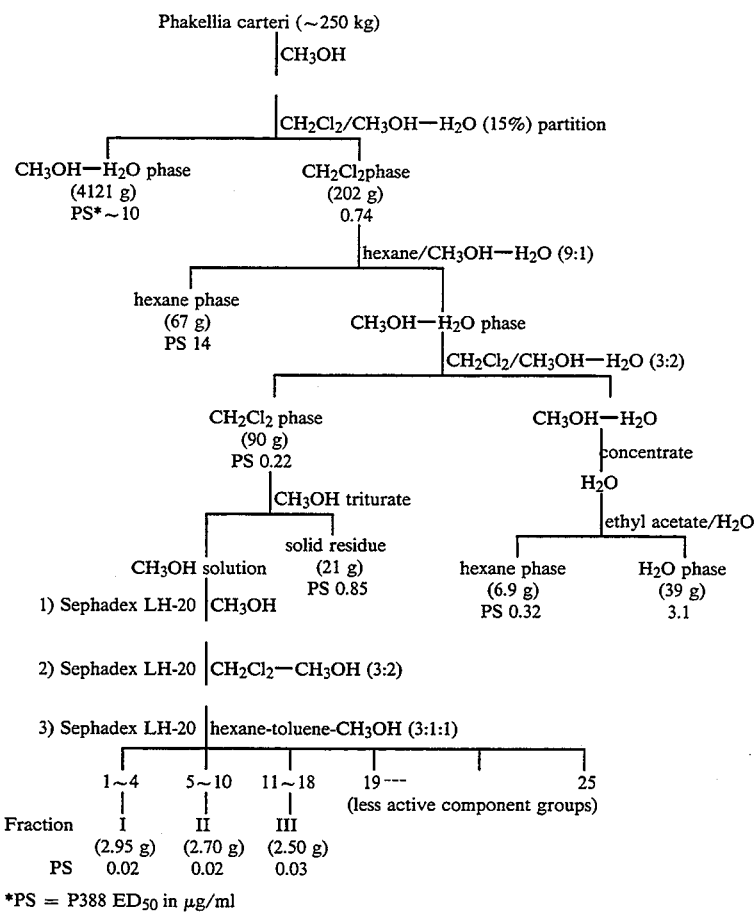

*PS = P388 ED$_{50}$ in μg/ml

SCHEME 2

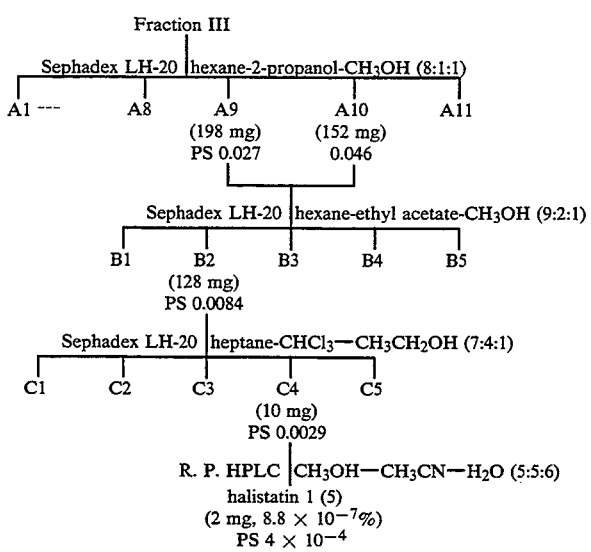

Another alternative source for halistatin 1 was discovered later. This second source for halistatin 1 is the Western Indian sponge *Axinella Carteri*. Halistatin 1 was extracted therefrom in the following manner.

A 1989 collection (600 kg. wet wt) of the erect orange sponge *Axinella carteri* (in methanol) was made. It was extracted with methanol-dichloromethane, and the chlorocarbon fraction was partitioned in methanol-water (9:1→3:2) between hexane→dichloromethane. The resulting PS cell line active (ED$_{50}$ 0.30 μg/ml) dichloromethane fraction was then separated by a series of gel permeation and partition column chromatographic steps on SEPHADEX LH-20, followed by HPLC on RP-8 reversed phase silica gel in accordance with Scheme 1 shown above.

*Sponge Extraction and Solvent Partition*—The methanol shipping solution from approximately 600 kg (wet wt.) of *Axinella carteri* was decanted and to the solution was added an equal volume of dichloromethane (~600 l) and enough (10-20% by volume) water to provide two phases. The dichloromethane layer was separated and solvent evaporated in vacuo to yield the first extract (1.43 kg). To the sponge was added 1:1 dichloromethane-methanol (550 l.). After 28 days water (15% by volume) was added to produce a chlorocarbon phase which was separated and concentrated (in vacuo) to obtain the second extract (1.66 kg). Recovered dichloromethane was combined with the upper layer (methanol/water) to form a dichloromethane-methanol-water solvent mixture (approximately 2:3.8:1.2) that was returned to the sponge to obtain the third dichloromethane extract fraction (607 g) in an analogous manner (18-32 day extraction periods). The combined dichloromethane extract (3.7 kg) was dissolved in a mixture (20 l. each) of hexane and 9:1 methanol-water and extracted (six times) with hexane in a 55 l steel container. The hexane fraction was concentrated at 30° C. and then the temperature was raised to 50° C. to remove water. The dark oily residue weighed 1.65 kg. The 9:1 methanol-water solution was filtered (filter paper) and the tan precipitate collected ($ED_{50}$ >100 µg/ml). The solution was diluted to 3:2 by adding 12 l. of water and extracted with dichloromethane (20 l., 3×). Concentration in vacuo gave a 181 g fraction from the chlorocarbon extract and a 493 g fraction from the methanol-water. Bioassay results (PS $ED_{50}$ 0.30 µg/ml pointed to the dichloromethane residue as the repository of the antineoplastic constituents. The PS cell line active fraction (181 g) was subjected to separation by gel permeation through a SEPHADEX LH-20 column (15×120 cm) packed in methanol. The column was eluted with methanol (25 l.) and fractions were monitored by the P388 cell line bioassay. The active fractions (3) were added to the top of another SEPHADEX LH20 column (9×92 cm) in dichloromethane-methanol (3:2) and eluted with the same solvent. Active fractions were further separated by SEPHADEX LH-20 column (4.5×80 cm) partition chromatography using 95:5 dichloromethane-methanol as eluent. The resulting active fraction was next separated on a SEPHADEX LH-20 column (2.5×40 cm) using the solvent system 8:1:1 cyclohexane-isopropanol-methanol.

Solvents used for column chromatography were redistilled. SEPHADEX LH-20, particle size 25-100 µm, used in column chromatographic separation was obtained from Pharmacia Fine Chemicals AB, Uppsala, Sweden. The TLC plates were from Analtech, Inc. The TLC plates were viewed under short wave (250 nm) uv-light first and then sprayed with ceric sulfate in 3N sulfuric acid followed by heating at approximately 150° C. For HPLC separations, the following conditions were used: Phenomenex Prepex RP-8 Reverse Phase semi preparative column (10.0×250 mm, particle size 5-20 µ); acetonitrile-methanol-water (5:5:6) as eluting solvent; Altex 110A pump controlled by Axxiom micro computer; Rainin RI-1 refractive index detector, range 32, and time constant 0.25. The flow rate (0.8 or 1.0 ml/min) and sample (1.0 to 4.0 mg) injection varied as noted. The $^1$H-NMR, APT, $^1$H-$^1$H COSY, $^1$H-$^{13}$C COSY, nOe and $^{13}$C-NMR experiments were carried out using a Bruker AM-400 NMR spectrometer equipped with cryomagnet and ASPECT-3000 computer. The HMBC spectra were recorded with a VARIAN 500 NMR spectrometer. The optical rotations were measured with a PERKIN-ELMER 241 polarimeter.

BRIEF DESCRIPTION OF DRAWINGS

Biological Testing; Data Display and Analysis; Screening Data Summary. Halistatin 1 was tested in the NCI's human tumor, disease-oriented in vitro primary screen, and data calculations performed. FIG. 1 is a composite prepared from mean graphs constructed from the averaged GI50 values from quadruplicate screenings of halistatin 1.

The averaged negative log10 GI50 values obtained for each cell line with halistatin 1 in the present study are provided as follows, along with the individual cell line identifiers: CCRF-CEM (9.43), HL-60TB (9.48), K-562 (9.44), MOLT-4 (9.21), RPMI-8226 (9.32), SR (9.77); A549/ATCC (8.54), EKVX (8.33), HOP-18 (8.00), HOP-62 (9.08), HOP-92 (8.96), NCI-H226 (9.09), NCI-H23 (9.24), NCI-H322M (8.46), NCI-H460 (9.40), NCI-H522 (9.68), LXFL 529 (9.32); DMS 114 (9.48), DMS 273 (9.54); COLO 205 (9.37) , DLD-1 (8.92), HCC-2998 (8.89), HCT-116 (9.30), HCT-15 (8.38), HT29 (9.38) , KM12 (9.24) , KM20L2 (9.28) , SW-620 (9.40); SF-268 (8.66), SF-295 (9.96), SF-539 (9.44); SNB-19 (8.64), SNB-75 (9.54), SNB-78 (9.32), U251 (9.29), XF 498 (9.32); LOX IMVI (10.09) , MALME-3M (9.68), M14 (9.21), M19-MEL (9.54), SK-MEL-2 (9.54), SK-MEL-28 (9.11), SK-MEL-5 (9.80), UACC-257 (9.07), UACC-62 (9.57); IGROV1 (9.08), OVCAR-3 (9.60), OVCAR-4 (8.15), OVCAR-5 (9.31), OVCAR-8 (8.72), SK-OV-3 (9.33); 786-0 (9.16), A498 (8.85), ACHN (8.49), CAKI-1 (8.80), RXF-393 (9.52), SN12C (8.66), TK-10 (8.22), UO-31 (8.21).

Halistatin 1 when tested against P388 lymphocytic leukemia in vivo resulted in a 100% survival rate at 40 µg/kg host body weight in BDF, mice using NCI protocol as described by Geran et al (1972) *Cancer Chemotherapy Reports,* Part 3, 3, pp. 1-103.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. An essentially pure composition of matter having the structural formula shown below, said composition denominated herein as halistatin 1:

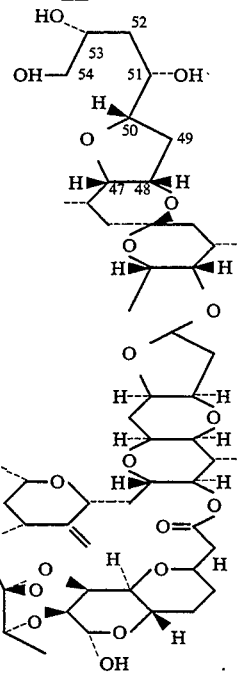
* * * * *